United States Patent [19]

Latta

[11] Patent Number: 5,587,163

[45] Date of Patent: Dec. 24, 1996

[54] LIQUID MIXTURE FOR INTERNAL USE, FOR PROPHYLACTIC HEALTH PROTECTION

[76] Inventor: Bernd Latta, Im Siekerfeld 1, D-33604 Bielefeld, Germany

[21] Appl. No.: 375,964

[22] Filed: Jan. 20, 1995

[30] Foreign Application Priority Data

Jan. 20, 1994 [DE] Germany ............................. 9400883 U
Feb. 10, 1994 [DE] Germany ............................. 9402223 U

[51] Int. Cl.⁶ .................................................. A61K 35/78
[52] U.S. Cl. ........................................ 424/195.1; 514/917
[58] Field of Search .......................... 424/195.1; 514/917

[56] References Cited

U.S. PATENT DOCUMENTS 4,770,880  9/1988  Sasaki et al. ......................... 424/195.1
4,963,356  10/1990  Calenoff et al. ......................... 424/91

*Primary Examiner*—John W. Rollins
*Attorney, Agent, or Firm*—Herbert L. Lerner; Laurence A. Greenberg

[57] ABSTRACT

A liquid mixture for internal use for prophylactic health protection is based on the active ingredients of biological natural products and is used in particular for prophylactic protection against the negative consequences of the effects of radiation, such as x-rays and the like, on the human organism. The liquid mixture includes a mixture of cellular liquid brewer's yeast and juice from foods, as well as a neutral liquid diluting the mixture.

4 Claims, No Drawings

LIQUID MIXTURE FOR INTERNAL USE, FOR PROPHYLACTIC HEALTH PROTECTION

BACKGROUND OF THE INVENTION

Field of the Invention

The invention relates to a liquid mixture for internal use for prophylactic health protection which is based on the active ingredients of biological natural products and is used in particular for prophylactic protection against the negative consequences of the effects of radiation, such as X-rays and the like, on the human organism.

Numerous causes of illness in the human body are due to the effects of deficiencies, such as vitamin deficiency. The prophylaxis of illness by increasing the defensive powers of the body itself, by supplying active ingredients that exist in nature, by now has gained increasing popularity in wide segments of the public. On one hand, a great many products are therefore known that are based on the illness-preventing action of vitamins or natural products that contain vitamins and are employed in health care.

In medicine, on the other hand, radiation, such as X-rays, are used for numerous examination methods as well as for radiation therapy. Although such examination methods have excellent significance in the treatment of illnesses, in excessive doses they are also highly harmful to health. Additionally, such harmful radiation also includes the radiation that occurs from human intervention into the natural environment, with an example being the ultraviolet radiation from sunlight. The biological effect of such radiation, in an excessive dose or with long-term action, can cause disruptions in the function and structure of the cellular tissue or organs and eventually can involve the entire organism. Known methods of radiation protection by keeping the threatened parts far away, or keeping them covered with material that is impermeable to radiation, can often not be employed reliably.

SUMMARY OF THE INVENTION

It is accordingly an object of the invention to provide a liquid mixture for internal use in humans, for prophylactic health protection, which overcomes the hereinafore-mentioned disadvantages of the heretofore-known products of this general type, which is based on active ingredients contained in biological natural products, which serves the purpose of both natural health care and in general of prophylactic health protection, and which also finds a use in the prophylaxis of damage resulting from the action on the human body of X-rays and other types of radiation.

With the foregoing and other objects in view there is provided, in accordance with the invention, a liquid mixture for internal use for prophylactic health protection, based on the active ingredients of biological natural products, in particular for prophylactic protection against the negative consequences of the effects of radiation, such as x-rays and the like, on the human organism, comprising a mixture of cellular liquid brewer's yeast and juice from foods; and a neutral liquid diluting the mixture.

In accordance with another feature of the invention, the juice from foods is selected from the group consisting of the juice of grasses, herbs, fruits, roots, vegetables, seeds and germs.

In accordance with a further feature of the invention, the mixture includes a proportion of 70 to 85% cellular liquid brewer's yeast, 1.5 to 3% green juice of wheat grass, 1.5 to 3% green juice of dandelion greens, and 15 to 22% lemon or lime juice.

Due to the natural active ingredients contained in the products mentioned, such as a broad spectrum of vitamin B and other vitamins as well as trace metals, it has been possible to demonstrate a pronounced effect in health care, in general prophylaxis against various disease phenomena and in particular in the prophylaxis of damage to the human organism caused by harmful radiation or excessive radiation doses in the composition proposed according to the invention.

In accordance with an added feature of the invention, the mixture includes a proportional composition of 78% cellular liquid brewer's yeast, 1.5% each of fresh green juice of wheat grass and fresh green juice of dandelion leaves, and 19% lemon or lime juice; and the neutral liquid dilutes the mixture in a form which is ready to drink in a proportion of the mixture to the liquid of approximately 1:0.5 to 1:1.

In accordance with a concomitant feature of the invention, the diluting liquid is uncarbonated natural mineral water.

Other features which are considered as characteristic for the invention are set forth in the appended claims.

Although the invention is described herein as embodied in a liquid mixture for internal use, for prophylactic health protection, it is nevertheless not intended to be limited to the details shown, since various modifications and structural changes may be made therein without departing from the spirit of the invention and within the scope and range of equivalents of the claims.

The content and method of preparation of the invention, however, together with additional objects and advantages thereof will be best understood from the following description of specific examples.

Referring now to a preferred embodiment of the invention, 2 ml of fresh green juice of wheat grass and 2 ml of fresh green juice of the leaves of dandelion are added to approximately 70 ml of cellular liquid brewer's yeast, and well stirred together with the addition of half the juice of a sun-ripened lime. This mixture is supplemented with from 110to 150 ml of uncarbonated mineral water and is then ready in beverage form for use in prophylactic health care.

I claim:

1. A liquid mixture for internal use for prophylactic health protection, based on the active ingredients of biological natural products, comprising:

a mixture of liquid brewer's yeast and a juice selected from the group consisting of the juice pressed from grasses, herbs, fruits, roots, vegetables, seeds and germs; and a substantially inert liquid diluting said mixture.

2. The liquid mixture according to claim 1, wherein said diluting liquid is uncarbonated natural mineral water.

3. A liquid mixture for internal use for prophylactic health protection, based on the active ingredients of biological natural products comprising:

a mixture having a proportion of 70 to 85% liquid brewer's yeast, 1.5 to 3% green juice of wheat grass, 1.5 to 3% green juice of dandelion greens, and 15 to 22% lemon or lime juice; and a substantially inert liquid diluting said mixture.

4. The liquid mixture according to claim 1, wherein said mixture includes a proportional composition of 78% liquid brewer's yeast, 1.5% each of green juice of wheat grass and green juice of dandelion leaves, and 19% of lemon or lime juice; and said neutral liquid dilutes said mixture in a proportion of said mixture to said liquid of approximately 1:0.5 to 1:1.

* * * * *